United States Patent [19]

Weber et al.

[11] 4,179,336
[45] Dec. 18, 1979

[54] MICROBIOLOGICAL DEGRADATION OF STEROL SIDE CHAINS TO A 17-KETO GROUP

[75] Inventors: Alfred Weber; Mario Kennecke; Helmut Dahl, all of Berlin, Fed. Rep. of Germany

[73] Assignee: Schering Aktiengellschaft, Bergkamen and Berlin, Fed. Rep. of Germany

[21] Appl. No.: 813,391

[22] Filed: Jul. 6, 1977

[30] Foreign Application Priority Data

Jul. 16, 1976 [DE] Fed. Rep. of Germany ....... 2632677

[51] Int. Cl.$^2$ ............................................. C07B 29/02
[52] U.S. Cl. ..................................... 435/55; 435/863
[58] Field of Search ....................................... 195/51 G

[56] References Cited

U.S. PATENT DOCUMENTS

| | | | |
|---|---|---|---|
| 3,451,892 | 6/1969 | Herzog et al. | 195/51 G |
| 3,684,656 | 8/1972 | Waard | 195/51 G |

OTHER PUBLICATIONS

Buki et al., Acta Microbiol. Acad. Sci., Hung. 22, 447–451 (1975).

*Primary Examiner*—Alvin E. Tanenholtz
*Attorney, Agent, or Firm*—Millen & White

[57] ABSTRACT

The side chains of sterols are degraded by fermentation with microorganisms capable of doing so in an improved manner by employing in such fermentations sterol derivatives of the formula

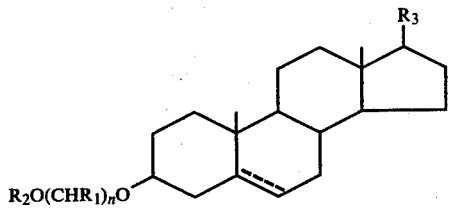

wherein n is 1 or 2; $R_1$ is H or lower alkyl, $R_2$ is alkyl, whose chain optionally is interrupted by an oxygen atom, or when n is 2, also a hydrogen atom; and $R_3$ is a sterol side chain.

10 Claims, No Drawings

MICROBIOLOGICAL DEGRADATION OF STEROL SIDE CHAINS TO A 17-KETO GROUP

BACKGROUND OF THE INVENTION

This invention relates to an improved process for the microbiological degradation of sterol side chains to a 17-keto group.

It is known that numerous microorganisms, for example, those of the genera Arthrobacter, Brevibacterium, Microbacterium, Protaminobacter, Bacillus, Nocardia, Streptomyces, and particularly Mycobacterium, can degrade the side chain of zoosterols and phytosterols. However, the degradation of the sterols continues to carbon dioxide and water, with 4-androstene-3,17-dione and 1,4-androstadiene-3,17-dione being formed only as intermediary products.

Since numerous zoosterols and phytosterols, e.g., cholesterol, stigmasterol, campesterol, brassicasterol and the sitosterols, are common in nature and accordingly are readily available starting materials for the synthesis of pharmacologically active steroids, numerous investigations have been conducted to control the degradation of the sterols so that during the fermentation a further degradation of the intermediately formed 4-androstene-3,17-dione and of the 1,4-androstadiene-3,17-dione is prevented.

Thus, it has been found possible, for example, to prevent the further degradation of 1,4-androstadiene-3,17-dione and 4-androstene-3,17-dione by adding inhibitors to the fermentation batches. See German Unexamined Laid-Open Applications DOS No. 1,543,269 and No. 1,593,327, as well as U.S. Pat. No. 1,208,078. By the use of inhibitors, however, conducting these reactions on a commercial scale becomes very expensive, due in part to the fact that the inhibitors employed must be removed from the fermentation cultures after the reaction has taken place, in order to avoid discharge of these materials into the waste-waters. Moreover, these conventional reactions have the disadvantage that during such processes the products in all cases are 1,4-androstadiene-3,17-dione or a mixture thereof and 4-androstene-3,17-dione and 1,4-androstadiene-3,17-dione is relatively unsuitable as a starting compound for the synthesis of pharmacologically effective steroids.

The further degradation of 1,4-androstadiene-3,17-dione and 4-androstene-3,17-dione can also be prevented by using mutated microorganisms of the genus Mycobacterium for the fermentative conversion of the sterols (see U.S. Pat. No. 3,684,657). The heretofore grown mutants, however, have the disadvantage that they have an only very limited capability of forming 1,4-androstadiene-3,17-dione or 4-androstene-3,17-dione from sterols.

Accordingly, it is an object of this invention to provide a process for the side chain degradation of sterols which lacks the disadvantages of the conventional methods. This object is met by the process of this invention, which employs specific sterol derivatives in the fermentation with a microorganism culture capable of the side chain degradation of sterols.

SUMMARY OF THE INVENTION

This invention relates to a process for the microbiological degradation of the side chain of a sterol to a 17-keto group which comprises employing as the starting sterol whose side chain is subjected to microbiological degradation a sterol 3-acetal or 3-ether of the formula $R_2O(CHR_1)_nO$— wherein n is 1 or 2, $R_1$ is H or lower alkyl and $R_2$ is alkyl whose chain optionally is interrupted by an oxygen atom or, when n is 2, also H.

More specifically, this invention relates to a process for the production of androstan-17-one derivatives of general Formula I

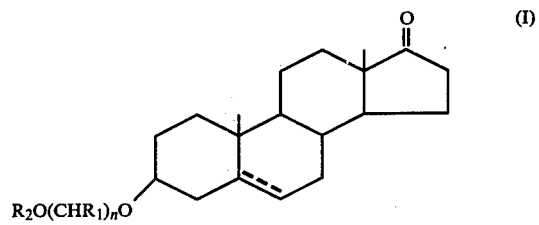

wherein $\equiv$ is a single bond or a double bond; n is the integer 1 or 2; $R_1$ is a hydrogen atom or a lower alkyl; and $R_2$ is alkyl whose chain optionally is interrupted by an oxygen atom or, when n is 2, also a hydrogen atom, which comprises subjecting a sterol derivative of general Formula II

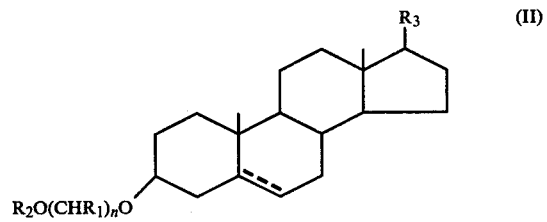

wherein $\equiv$, n, $R_1$ and $R_2$ have the values given above and $R_3$ is hydrocarbon of a sterol side chain of 8–10 carbon atoms, to the degradative activity of a microorganism which degrades sterol side chains.

DETAILED DISCUSSION

It is very surprising that during this fermentative conversion, the androstan-17-one derivatives of general Formula I are formed in high yields because it is known that the side chain degradation of sterols is accomplished by a very complex fermenting system. It could not, therefore, be anticipated that all of the enzymes involved in the microbiological degradation of the side chain of natural steroids would also be able to effect the side chain degradation of the sterol derivatives of general Formula II, which do not occur in nature. Moreover, it could not be predicted that these enzyme systems, which are capable of degrading 1,4-androstadiene-3,17-dione and of 4-androstene-3,17-dione to carbon dioxide and water, are incapable of degrading androstan-17-one derivatives of general Formula I.

In the above formulae, when one or both of $R_1$ and $R_2$ is alkyl, alkyl is preferably of 1–4 carbon atoms, e.g., propyl, butyl, isopropyl, sec.-butyl, and especially methyl and ethyl. When n is 2, at least one and preferably both $R_1$ groups are H. When $R_2$ is alkyl whose chain is interrupted by an oxygen atom, it preferably is of 3–6 carbon atoms, e.g., alkyloxyalkylene, wherein alkyl is as defined above and alkylene is of 2–4 carbon atoms, preferably 2-alkoxyethylene, e.g., 2-methoxyethylene or 2-ethoxyethylene.

Contemplated equivalents of the foregoing $R_1$ and $R_2$ groups are those wherein $R_1$ or $R_2$ or both are alkyl of more than 4 carbon atoms, e.g., 5, 6, 7, 8 or more carbon atoms and those wherein $R_2$ is alkyl interrupted by more than one oxygen atom, e.g., of the formula alkyl-$(-O-\text{alkylene})_m-$ and $H(-O-\text{alkylene})_m-$, wherein m is an integer greater than 1, e.g., 2, 3 or more, and alkyl and alkylene are as defined above, the latter preferably being ethylene, propylene or trimethylene, such compounds terminating in a hydroxy group being produced by the reaction of ethylene oxide, propylene oxide and trimethylene oxide, respectively, with a melt or solution in an inert solvent of the 3-hydroxy sterol and a catalytic amount of sodium, which products can then be etherified with the selected alkanol.

$R_3$ is a hydrocarbon group of 8–10 carbon atoms, more specifically the hydrocarbon 17-side chain of a naturally occurring zoo- or phytosterol, e.g., cholesterol, stigmasterol, campesterol, brassicasterol, or the sitosterols.

Examples of sterol derivatives of general Formula II are those of general Formulae IIa and IIb

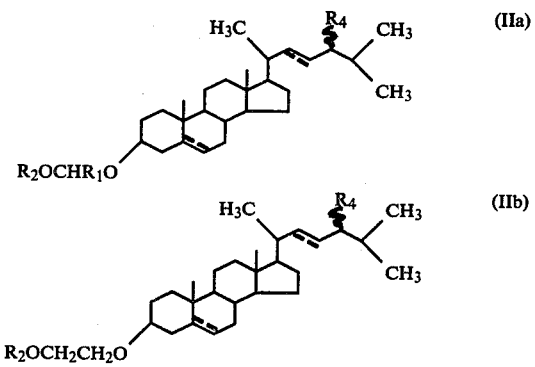

wherein $R_1$ and $R_2$ have the values given above, $=\!=\!=$ is a single or double bond, and $R_4$ is a hydrogen atom, methyl or ethyl.

Especially suitable sterol derivatives of general Formulae IIa and IIb are the $\Delta^5$-steroids and the 5α-sterol derivatives of these formulae.

Apart from the use of a different starting steroid and the fact that the reaction can be conducted in the absence of inhibitors, the process of this invention can be conducted under the same fermentation conditions which are conventionally employed in the microbiological side chain degradations of sterols.

Thus, the fermentation is conducted using the microorganism cultures customarily utilized for the side chain degradation of sterols. Suitable cultures are, for example, those bacterial cultures which are capable of degrading the side chain of sterols, e.g., the genera Arthrobacter, Brevibacterium, Microbacterium, Protaminobacter, Streptomyces, or particularly the genus Mycobacterium. Specific examples are *Microbacterium lactum* IAM-1640; *Protaminobacter alboflavus* IAM-1040; *Bacillus roseus* IAM-1257; *Bacillus sphaericus* ATCC-7055; *Nocardia gardneri* IAM-105; *Nocardia minima* IAM-374; *Nocardia corallina* IFO-3338; *Streptomyces rubescens* IAM-74; or particularly the microorganisms *Mycobacterium avium* IFO-3082; *Mycobacterium phlei* IFO-3158; *Mycobacterium phlei* (Institute of Health, Budapest No. 29); *Mycobacterium phlei* ATCC-354; *Mycobacterium smegmatis* IFO-3084; *Mycobacterium smegmatis* ATCC-20; *Mycobacterium smegmatis* (Institute of Health, Budapest No. 27); *Mycobacterium smegmatis* ATCC-19979; *Mycobacterium fortuitum* CBS-49566; *Mycobacterium* spec. NRRL-B-3805; and *Mycobacterium* spec. NRRL-B-3683.

Using the culturing conditions conventionally employed with these microorganisms, submerged cultures are grown in a suitable nutrient medium under aeration. The steroid substrate, ordinarily dissolved in a suitable solvent or preferably in emulsified form, is added to the culture and fermentation is continued, preferably until a maximum substrate conversion has been achieved.

Typical substrate solvents are, for example, methanol, ethanol, glycol monomethyl ether, dimethylformamaide or dimethyl sulfoxide. The emulsification of the substrate can be accomplished, for example, by adding the substrate in micronized form or dissolved in a water-miscible solvent, e.g., methanol, ethanol, acetone, glycol monomethyl ether, dimethylformamide, or dimethyl sulfoxide, under turbulent mixing conditions through a nozzle into preferably decalcified water containing the customary emulsifiers. Suitable emulsifiers are nonionic emulsifiers, such as, for example, ethylene oxide adducts or fatty acid esters of polyglycols. Specific examples of suitable emulsifiers are the commercial surfactants "Tegin," "Tagat," "Tween," and "Span."

Frequently, the emulsification of the steroid substrate makes if possible to achieve an increased substrate throughput and thus an increase in substrate concentration. However, it is also possible to utilize in the process of this invention other methods for increasing the substrate throughput, as they are well-known to persons skilled in the art of microbiological conversions of steroids.

The fermentation is conducted under conventional conditions (G. S. Forken and R. A. Johnson, "Chemical Oxidations With Microorganisms," Macel Dekker, Inc., New York, 1972).

The optimums of substrate concentration, time of substrate addition and duration of fermentation are dependent on the structure of the substrate employed and on the type of microorganism utilized. These variables must be determined, as generally required in microbiological steroid conversions, in each individual case by preliminary experiments, which are well-known to those skilled in the art.

As is known in the art, a usually less preferred alternative to conducting the fermentation in the presence of the steroid substrate is to contact the steroid with the enzymes produced by the fermentation of the microorganism, in the absence of the organism itself.

The androstan-17-one derivatives of general Formula I produced by the process of this invention are valuable intermediates for the production of pharmacologically active steroids.

Thus, it is possible, for example, to cleave the 3-acetals of Formula I (n=1), viz., androstan-17-ones of general Formula Ia

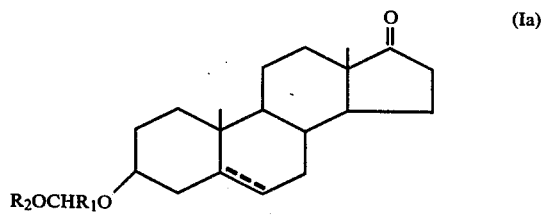

wherein $=\!=\!=$, $R_1$ and $R_2$ have the values given above, in the presence of $H^+$ ions or Lewis acids to produce 3β-hydroxy-5-androsten-17-one and 3β-hydroxy-5α-androstan-17-one, respectively, employing conditions conventionally employed for the hydrolysis or alcoholysis of acetals. Thus, it is possible, for example, to cleave the compounds by reaction in a lower alcohol, e.g., methanol or ethanol, or in an aqueous organic solvent, e.g., glycol monomethyl ether, tetrahydrofuran, dioxane, dimethylformamide, dimethyl sulfoxide, hexamethylphosphoric triamide, acetone, with a mineral acid, e.g., hydrochloric acid, sulfuric acid, phosphoric acid, perchloric acid, a sulfonic acid, e.g., p-toluenesulfonic acid, a strongly acidic carboxylic acid, e.g., formic acid, acetic acid, trifluoroacetic acid, an acidic ion exchanger, or with a Lewis acid, e.g., boron trifluoride, zinc chloride or zinc bromide.

It is thus possible to prepare 3β-hydroxy-5-androsten-17-one by a simple process. As is known, the esters of this known compound are pharmacologically active. (Chem. Abstr. 65 [1966]:12264f and DOS No. 1,643,046).

It is likewise possible to reduce the androstan-17-one derivatives of general Formula Ia in the 17-position or to alkylate them with an organometallic compound of the general Formula IV $$MeR_5 \quad (IV)$$

wherein $R_5$ is saturated or unsaturated hydrocarbon of up to 2 carbon atoms and Me is an alkali metal atom or a magnesium halide group, i.e., MgCl or MgBr.

The thus-produced compounds of general Formula III

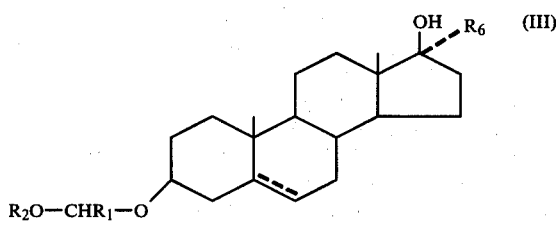

wherein $\equiv\equiv\equiv$, $R_1$ and $R_2$ have the values given above and $R_6$ is either $R_5$ as defined above or is a hydrogen atom, can be hydrolyzed in the presence of H+ ions or a Lewis acid to the corresponding 3β-hydroxy compounds. The conversion of these compounds into pharmacologically active steroids can be accomplished in a conventional manner.

For example, the 3β-hydroxy-5-androsten-17-one derivatives obtained in this way can be converted by means of an Oppenauer reaction (for example, by heating the hydrolysis products in benzene-acetone with aluminum isopropylate) into the corresponding 17β-hydroxy-3-keto-Δ4-steroids, such as, for example, testosterone, 17α-methyltestosterone, 17α-ethyltestosterone, or 17α-ethynyltestosterone which, as is known, possess a pronounced male hormone activity.

Moreover, the compounds 17α-ethynyl-17β-hydroxy-4-androsten-3-one and 17β-hydroxy-17α-vinyl-4-androsten-3-one are, as is known, valuable intermediates for the preparation of the pharmacologically effective 17α-hydroxyprogesterone and the esters thereof (Helv. Chim. Acta 24 [1941]: 945 and DOS No. 2,140,291).

The reduction of the 17-keto group of the 5-androsten-17-one derivatives of general Formula I can be accomplished by methods well known to those skilled in the art (see, for example, John Fried: Organic Reactions in Steriod Chemistry, van Nostrand Reinhold Comp., New York etc. 1972, Vol. 1, pp. 61 et seq.). For example, these compounds can be reacted with sodium boro-hydride or lithium aluminum hydride, to obtain the corresponding 17β-hydroxy-5-androstene derivatives.

The methods for alkylating the 17-keto group are likewise conventional (see, for example, John Fried: Organic Reactions in Steriod Chemistry, van Nostrand Reinhold Comp., New York etc. 1972, Vol. 2, pp. 53 et seq.). For example, the 5-androsten-17-one derivatives of general Formula I can be reacted with alkyl magnesium halides or alkali metal acetylides, thus obtaining the corresponding 17β-hydroxy-17α-alkyl- (or -ethynyl-) 5-androstene derivatives.

The androstan-17-one derivatives of general Formula Ib produced from the sterol derivatives of general Formula IIb,

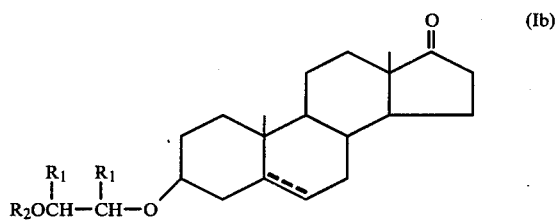

wherein $\equiv\equiv\equiv$, $R_1$ and $R_2$ have the values given above, can be converted, for example, by reaction with acyl anhydrides or acyl chlorides in the presence of boron trifluoride into the corresponding 3β-acyloxy esters.

It is also possible to hydrogenate the 5-androsten-17-one derivatives to the corresponding 5α-androstan-17-one derivatives. Depending on the selected reaction conditions, the 17-oxo group can be preserved or reduced to the corresponding 17β-hydroxy group in these reactions.

The 5α-androstan-17-one derivatives of general Formulae I, Ia and Ib, can, for example, be converted into the corresponding 17β-acyloxy-5α-androstan-3-ones, after reduction of the 17-keto group to the 17β-hydroxy group, esterification of the latter, cleavage of the 3-acetal or 3-ether bond, and oxidation of the 3-hydroxy group; these 17β-acyloxy-5α-androstan-3-ones are, as is known, anabolically active compounds (Endocrinologie [Endocrinology] 66 [1960]: 13).

The starting compounds for the process of this invention are known or can be produced with the use of conventional methods (J. Pharm. Soc. 54: 514 [1965]; Can. J. Chem. 49: 2418 [1971]; Synthesis 1975: 276 and 1976: 244; Tetrahedron Letters 1976: 809; Can. J. Chem. 50: 2788 [1972]; and Bull. Soc. Chim. France 1960: 297).

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

(A) Examples Relating to the Microbiological Side Chain Degradation

EXAMPLE 1

(a) An Erlenmeyer flask having a capacity of 750 ml. is charged with 200 ml. of a sterile nutrient solution containing 1% of yeast extract, 0.45% of disodium hydrogen phosphate, 0.34% of potassium dihydrogen phosphate, and 0.2% of "Tagat" 02 and adjusted to pH 6.7. The charge is inoculated with a supernatant broth of a dry culture of Mycobacterium spec. NRRL-B-3805 and shaken for 3 days at 30° C. with 190 r.p.m.

(b) A 50-liter fermentor charged with 40 l. of a sterile nutrient solution containing 1.23% of yeast extract (65% strength), 0.68% of potassium dihydrogen phosphate, and 0.2% of "Tagat" 02—adjusted to pH 6.0—is inoculated with 200 ml. of the Mycobacterium spec. growth culture, and the subculture is incubated for 48 hours at 30° C. under aeration (2 m$^3$ per hour).

(c) 400 g. of cholesterol is dissolved in 6 l. of formaldehyde dimethylacetal, combined under agitation at room temperature with 400 g. of kieselguhr and in incremental portions with 200 g. of phosphorus pentoxide, and agitated for 2 hours at room temperature. The mixture is filtered off from the insoluble matter, washed with formaldehyde dimethylacetal, and the solvent is distilled off under vacuum. After the addition of sodium bicarbonate solution, the solid crude product is filtered off, washed with water, and the yield after drying is 440 g. of 3β-methoxymethoxy-5-cholestene. The compound, recrystallized from acetone, melts at 79°-80° C.

400 g. of the thus-prepared 3β-methoxymethoxy-5-cholestene is emulsified for 30 minutes with 120 g. of "Tegin," 10 l. of fully demineralized water, and 40 ml. of 1 N sodium hydroxide solution at 95° C. with a "Dispax" reactor DR-3-6-6 (company: Jahnke & Kunkel, Federal Republic of Germany). The emulsion is sterilized for 20 minutes at 120° C.

(d) A 50-liter fermentor is charged with 40 l. of a sterile nutrient solution containing 2.0% of corn steep liquor, 0.3% of diammonium hydrogen phosphate, and 0.25% of "Tagat" 02—adjusted to pH 6.5—and is inoculated with 2 l. of a Mycobacterium spec. subculture. The charge is incubated under aeration (0.5 m$^3$ per hour) and agitation (250 r.p.m.) for 24 hours at 30° C. Thereafter, the 3β-methoxymethoxy-5-cholestene emulsion produced in accordance with paragraph (c) is added to the culture, and the latter is fermented for another 120 hours.

After the fermentation has been completed, the culture is extracted three times with respectively 5 l. of ethylene chloride; the ethylene chloride extract is filtered and concentrated under vaccum.

The residue (156 g.) is chromatographed over a silica gel column, recrystallized from ethyl acetate, and the yield is 86 g. of 3β-methoxymethoxy-5-androsten-17-one, m.p. 129/131°-132° C.

EXAMPLE 2

(a) A 2-liter Erlenmeyer flask charged with 500 ml. of a sterile nutrient medium is used to cultivate Mycobacterium spec. NRRL-B-3805 under the conditions of Example 1(a).

(b) 10 g. of sitosterol is reacted as described in Example 1(c), thus obtaining 11 g. of 24-ethyl-3β-methoxymethoxy-5-cholestene. The compound, recrystallized from acetone, melts at 70°-71° C.

Ten grams of the thus-produced 24-ethyl-3β-methoxymethoxy-5-cholestene is emulsified with 4 g. of "Tegin" and 300 ml. of water at 95° C. in an "Ultra-Turrax" mixer (company: Jahnke & Kunkel, Federal Republic of Germany) for 10 minutes. The emulsion is sterilized for 20 minutes at 120° C.

(c) Twenty Erlenmeyer flasks with respectively 85 ml. of a sterile nutrient medium containing 2.0% of corn steep liquor, 0.3% of diammonium hydrogen phosphate, and 0.25% of "Tagat" 02—adjusted to pH 6.5—are each inoculated with 5 ml. of the Mycobacterium spec. growth culture and shaken for 24 hours at 30° C. and with 220 r.p.m.

Thereafter, each culture is combined with 14 ml. of the 24-ethyl-3β-methoxymethoxy-5-cholestene suspension (corresponding to 0.5 g. of 24-ethyl-3β-methoxymethoxy-5-cholestene) and fermented for another 120 hours at 30° C. on a shaker.

After the reaction mixture has been worked up as described in Example 1(d), 2.1 g. of 3β-methoxymethoxy-5-androsten-17-one is obtained, m.p. 130°-132° C.

EXAMPLE 3

(a) 10.5 g. of stigmasterol is reacted as described in Example 1(c), thus obtaining 10.75 g. of 24-ethyl-3β-methoxymethoxy-5,22-cholestadiene. The compound, recrystallized from acetone, melts at 103°-104° C.

(b) Under the conditions described in Example 2(b), 10 g. of 24-ethyl-3β-methoxymethoxy-5,22-cholestadiene is emulsified.

(c) Under the conditions set forth in Examples 2(a) and 2(c), 85 ml. of a Mycobacterium spec. NRRL-B-3805 culture is prepared and combined with 14 ml. of the 24-ethyl-3β-methoxymethoxy-5,22-cholestadiene suspension (corresponding to 0.5 g. of 24-ethyl-3β-methoxymethoxy-5,22-cholestadiene).

After another 120 hours of incubating at 30° C. on a shaker, the mixture is worked up as described in Example 1(d), thus obtaining 2.3 g. of 3β-methoxymethoxy-5-androsten-17-one, m.p. 130°-132° C.

EXAMPLE 4

(a) 20 g. of cholesterol is dissolved in 300 ml. of formaldehyde diethylacetal, combined under agitation at room temperature with 30 g. of kieselguhr and in incremental portions with 15 g. of phosphorus pentoxide, and agitated for 4 hours at room temperature. The product is filtered off from the insoluble matter, washed with formaldehyde diethylacetal, and the solvent is distilled off under vacuum. The residue is crystallized at 0° C. After adding sodium bicarbonate solution, the crude product is vacuum-filtered, washed with water, and, after drying, 22.5 g. of 3β-ethoxymethoxy-5-cholestene is obtained. The compound, recrystallized from ethyl acetate, melts at 64°-66° C.

(b) Under the conditions described in Example 2(b), 10 g. of 3β-ethoxymethoxy-5-cholestene is emulsified.

(c) Under the conditions set forth in Examples 2(a) and 2(c), 85 ml. of a Mycobacterium spec. NRRL-B-3805 culture is prepared and combined with 14 ml. of the 3β-ethoxymethoxy-5-cholestene suspension (corresponding to 0.5 g. of 3β-ethoxymethoxy-5-cholestene).

After another 120 hours of incubating at 30° C. on a shaker, the mixture is worked up as indicated in Example 1(d), thus obtaining 1.5 g. of 3β-ethoxymethoxy-5-androsten-17-one, m.p. 121°-123° C.

EXAMPLE 5

(a) 38.67 g. of cholesterol is dissolved in 250 ml. of methylene chloride and 164.2 g. of formaldehyde bisglycol monomethyl ether acetal (producible, for example, in accordance with DOS No. 2,405,633). Under agitation at room temperature, 60 g. of kieselguhr and 30 g. of phosphorus pentoxide are added thereto, and the mixture is stirred for one hour at room temperature. The product is filtered off from the insoluble matter, washed with methylene chloride, and neutralized with methanolic potassium hydroxide solution. After the solvents have been distilled off under vacuum, the mixture is taken up in methanol, filtered, and the compound is crystallized by gradual evaporation, thus obtaining 25 g. of 3$\beta$-(2,5-dioxahexyloxy)-5-cholestene, m.p. 41°–42° C.

(b) Under the conditions described in Example 2(b), 10 g. of 3$\beta$-(2,5-dioxahexyloxy)-5-cholestene is emulsified.

(c) Under the conditions set forth in Examples 2(a) and 2(c), 25 ml. of a Mycobacterium spec. NRRL-B-3805 culture is prepared and combined with 14 ml. of the 3$\beta$-(2,5-dioxahexyloxy)-5-cholestene suspension [corresponding to 0.5 g. of 3$\beta$-(2,5-dioxahexyloxy)-5-cholestene].

After a further 120 hours of incubating at 30° C. on a shaker, the mixture is worked up as described in Example 1(d), thus obtaining 1.75 g. of 3$\beta$-(2,5-dioxahexyloxy)-5-androsten-17-one, m.p. 65°–67° C.

EXAMPLE 6

(a) 12 g. of cholesterol is suspended in 100 ml. of acetaldehyde dimethylacetal, combined under agitation at room temperature with 25 g. of kieselguhr and in incremental portions with 12 g. of phosphorus pentoxide, and agitated for 45 minutes at room temperature. The product is filtered off from the insoluble matter, washed with methylene chloride, and the solution is neutralized with methanolic sodium hydroxide solution. After the solvents have been distilled off under vacuum, the crude product is recrystallized from acetone under the addition of active carbon, thus obtaining 10.2 g. of 3$\beta$-(1-methoxyethoxy)-5-cholestene, m.p. 94°–95° C.

(b) Under the conditions set forth in Example 2(b), 10 g. of 3$\beta$-(1-methoxyethoxy)-5-cholestene is emulsified.

(c) Under the conditions set forth in Examples 2(a) and 2(c), 85 ml. of a Mycobacterium spec. NRRL-B-3805 culture is prepared and combined with 14 ml. of the 3$\beta$-(1-methoxyethoxy)-5-cholestene suspension [corresponding to 0.5 g. of 3$\beta$-(1-methoxyethoxy)-5-cholestene]. After another 120 hours of incubating at 30° C. on a shaker, the mixture is worked up as indicated in Example 1(d), thus obtaining 1.89 g. of 3$\beta$-(1-methoxyethoxy)-5-androsten-17-one, m.p. 111°–118° C.

EXAMPLE 7

(a) 19.33 g. of cholesterol is combined in 200 ml. of methylene chloride with 23.6 ml. of vinyl ethyl ether and 86 mg. of p-toluenesulfonic acid (anhydrous), and agitated for 1.5 hours at room temperature. After neutralizing with sodium bicarbonate solution, the mixture is extracted with sodium chloride solution, dried with sodium sulfate, and the solvent is distilled off. The oily crude product is chromatographed with hexane-ethyl acetate mixtures on silica gel, thus obtaining 18.4 g. of 3$\beta$-(1-ethoxyethoxy)-5-cholestene as a colorless, waxy compound.

(b) Under the conditions described in Example 2(b), 10 g. of 3$\beta$-(1-ethoxyethoxy)-5-cholestene is emulsified.

(c) Under the conditions described in Examples 2(a) and 2(c), 85 ml. of a Mycobacterium spec. NRRL-B-3805 culture is prepared and combined with 14 ml. of the 3$\beta$-(1-ethoxyethoxy)-5-cholestene suspension [corresponding to 0.5 g. of 3$\beta$-(1-ethoxyethoxy)-5-cholestene]. Subsequently, the mixture is incubated for another 120 hours on a shaker (at 30° C.).

The combined cultures are extracted with ethylene chloride. The extracts are concentrated under vacuum, the residue is combined with 70 ml. of methanol, 12 ml. of water, and 6 ml. of concentrated HCl, and the mixture is heated under reflux for one hour. After cooling to 12° C., the reaction product is precipitated with 100 ml. of water and then filtered off. Recrystallization from acetone yields 0.62 g. of 5-androsten-3$\beta$-ol-17-one, m.p. 138/148°–149° C.

EXAMPLE 8

(a) 38.7 g. of cholesterol is dissolved in 500 ml. of methylene chloride, combined at 0° C. with 25 ml. of ethylene oxide, and 0.5 ml. of boron trifluoride etherate is added to the reaction mixture. The latter is allowed to stand overnight at room temperature, extracted with water, dried with sodium sulfate, and the solvent is distilled off under vacuum. The crude product (50 g.) is chromatographed on silica gel with hexane-ethyl acetate mixtures, thus obtaining 10 g. of 3$\beta$-(2-hydroxyethoxy)-5-cholestene, m.p. 91°–95° C.

(b) Under the conditions described in Example 2(b), 10 g. of 3$\beta$-(2-hydroxyethoxy)-5-cholestene is emulsified.

(c) Under the conditions set forth in Examples 2(a) and 2(c), 85 ml. of a Mycobacterium spec. NRRL-3805 culture is prepared and combined with 14 ml. of the 3$\beta$-(2-hydroxyethoxy)-5-cholestene suspension [corresponding to 0.5 g. of 3$\beta$-(2-hydroxyethoxy)-5-cholestene]. After another 120 hours of incubating at 30° C. on a shaker, the reaction mixture is worked up as set forth in Example 1(d), thus obtaining 2.1 g. of 3$\beta$-(2-hydroxyethoxy)-5-androsten-17-one, m.p. 173/175°–177° C.

EXAMPLE 9

(a) 20 g. of 5$\alpha$-cholestan-3$\beta$-ol is reacted, as disclosed in Example 1(c), with formaldehyde dimethylacetal, thus producing 21.5 g. of 3$\beta$-methoxymethoxy-5$\alpha$-cholestane. The compound, recrystallized from acetone, melts at 65°–68° C.

(b) Under the conditions described in Example 2(b), 10 g. of 3$\beta$-methoxymethoxy-5$\alpha$-cholestane is emulsified.

(c) Under the conditions indicated in Examples 2(a) and 2(c), 85 ml. of a Mycobacterium spec. NRRL-3805 culture is prepared and combined with 14 ml. of the 3$\beta$-methoxymethoxy-5$\alpha$-cholestane suspension (corresponding to 0.5 g. of 3$\beta$-methoxymethoxy-5$\alpha$-cholestane). After another 120 hours of incubating at 30° C. on a shaker, the mixture is worked up as set forth in Example 1(d), thus obtaining 2.05 g. of 3$\beta$-methoxymethoxy-5$\alpha$-androstan-17-one, m.p. 97°–98° C.

(B) Examples Relating to the Chemical Further Processing of the Androstan-17-one Derivatives

EXAMPLE 10

25 g. of the 3$\beta$-methoxymethoxy-5-androsten-17-one set forth in Examples 1–3 is heated for one hour under reflux with 125 ml. of methanol, 25 ml. of water, and 12.5 ml. of concentrated hydrochloric acid. The mixture is then cooled, extracted with water, and filtered off, thus obtaining 21.6 g. of 5-androsten-3β-ol-17-one, m.p. 148°–149° C. (from methanol).

EXAMPLE 11

0.5 g. of the 3β-ethoxymethoxy-5-androsten-17-one obtained in Example 4 is reacted under the conditions set forth in Example 10, thus producing 0.4 g. of 5-androsten-3β-ol-17-one, m.p. 148°–149° C. (from methanol).

EXAMPLE 12

0.38 g. of the 3β-(2,5-dioxahexyloxy)-5-androsten-17-one of Example 5 is reacted as in Example 10 and worked up. Crystallization from methanol yields 0.2 g. of 5-androsten-3β-ol-17-one, m.p. 148°–149° C.

EXAMPLE 13

One gram of the 3β-(1-methoxyethoxy)-5-androsten-17-one obtained in Example 6 is reacted under the conditions set forth in Example 10, but for one hour at room temperature, thus obtaining 0.8 g. of 5-androsten-3β-ol-17-one, m.p 148°–149° C. (from methanol).

EXAMPLE 14

One gram of the 3β-(2-hydroxyethoxy)-5-androsten-17-one obtained in Example 8 is combined in 5 ml. of methylene chloride with 5 ml. of acetic anhydride and 0.05 ml. of boron trifluoride etherate. After 4 hours at room temperature, water is added and the mixture is stirred for half an hour. After adding methylene chloride, the aqueous phase is separated and the organic phase is extracted with sodium bicarbonate solution. After drying and removal of the volatile components by distillation under vacuum, a residue is obtained which is purified by crystallization from methanol, thus producing 0.9 g. of 3β-acetoxy-5-androsten-17-one, m.p. 167°–170° C.

EXAMPLE 15

11 g. of potassium tert.-butylate in 100 ml. of tetrahydrofuran is converted into the acetylide by the introduction of acetylene. At 10° C., a solution of 20 g. of 3β-methoxymethoxy-5-androsten-17-one in 100 ml. of tetrahydrofuran is introduced into this suspension, and the latter is stirred for one hour. The solvent is distilled off under vacuum and replaced by water. The crude product is vacuum-filtered, washed with water, and dried, thus obtaining 21.53 g. of 17α-ethynyl-3β-methoxymethoxy-5-androsten-17β-ol, m.p. 184°–186° C. (from methanol).

EXAMPLE 16

3.59 g. of 17α-ethynyl-3β-methoxymethoxy-5-androsten-17β-ol is heated for 150 minutes under reflux with 100 ml. of acetone, 4 ml. of water, and 3.4 ml. of concentrated hydrochloric acid. After cooling, the product is precipitated with water, filtered off, washed with water, and dried, thus obtaining 3.1 g. of 17α-ethynyl-5-androsten-3β,17β-diol, m.p. 241°–243° C. (from acetone).

EXAMPLE 17

Methylmagnesium bromide is prepared from 1.5 g. of magnesium filings, 37.5 ml. of toluene, and 9 ml. of ether with gaseous methyl bromide in the usual manner. At room temperature and under a nitrogen atmosphere, a solution of 5.63 g. of 3β-methoxymethoxy-5-androsten-17-one in 40 ml. of toluene is introduced into this mixture within 30 minutes. The mixture is then stirred under nitrogen for 200 minutes at 50°–55° C., cooled off, gently combined with dilute sulfuric acid, and the solvents are distilled off and the crystals isolated. Yield: 5.85 g. of 3β-methoxymethoxy-17α-methyl-5-androstan-17β-ol, m.p. 134°–135° C. (from methanol).

EXAMPLE 18

3.49 g. of 3β-methoxymethoxy-17α-methyl-5-androsten-17β-ol is dissolved in 100 ml. of acetone, combined with 6 ml. of concentrated hydrochloric acid and 6 ml. of water, and heated under reflux for one hour. After cooling, the product is precipitated with water, filtered, washed with water, and dried, thus obtaining 3.0 g. of 17α-methyl-5-androstene-3β,17β-diol, m.p. 200°–204° C. (from methanol).

EXAMPLE 19

20 g. of 3β-methoxymethoxy-5-androsten-17-one is dissolved in 100 ml. of ethanol and 150 ml. of benzene, combined with 2.63 g. of sodium borohydride, and agitated for 2 hours at room temperature. Thereafter, the mixture is combined with water, the solvents are distilled off under vacuum, and the crude product is vacuum-filtered, washed with water, and dried, thus obtaining 20.1 g. of 3β-methoxymethoxy-5-androsten-17β-ol, m.p. 149°–150° C. (from methanol).

EXAMPLE 20

5 g. of 3β-methoxymethoxy-5-androsten-17β-ol is combined in 40 ml. of pyridine with 2 ml. of benzoyl chloride and allowed to stand overnight. The mixture is then precipitated into ice water, the crystals are vacuum-filtered, washed with water, and dried, thus producing 6.55 g. of 17β-benzoyloxy-3β-methoxymethoxy-5-androstene, m.p. 165°–166° C. (from methanolmethylene chloride).

EXAMPLE 21

0.395 g. of 17β-benzoyloxy-3β-methoxymethoxy-5-androstene is heated under reflux for 5 hours with 4 ml. of tetrahydrofuran, 1 ml. of distilled water, and 0.1 ml. of concentrated hydrochloric acid. The solvents are distilled off and the crystals are vacuum-filtered, thus obtaining 0.355 g. of 17β-benzoyloxy-5-androsten-3β-ol, m.p. 210°–213° C. (from methanol).

EXAMPLE 22

Five grams of 3β-methoxymethoxy-5α-androstan-17-one is reduced with sodium borohydride as described in Example 19, thus obtaining 5 g. of 3β-methoxymethoxy-5α-androstan-17β-ol, m.p. 110°–112° C. (from methanol).

EXAMPLE 23

Two grams of 3β-methoxymethoxy-5α-androstan-17β-ol is esterified with benzoyl chloride as described in Example 20, thus obtaining 2.5 g. of 17β-benzoyloxy-3β-methoxymethoxy-5α-androstane, m.p. 118°–120° C. (from methanol).

EXAMPLE 24

One gram of 17β-benzoyloxy-3β-methoxymethoxy-5α-androstane is heated under reflux for 2 hours with 10 ml. of tetrahydrofuran, 2 ml. of water, and 1 ml. of concentrated hydrochloric acid. After cooling, 50 ml. of water is added to the mixture; the crystallized product is vacuum-filtered, washed with water, and dried, thus obtaining 0.89 g. of 17β-benzoyloxy-5α-androstan-3-ol, m.p. 192°–195° C.

EXAMPLE 25

Two grams of 17β-benzoyloxy-3β-methoxymethoxy-5-androstene is hydrogenated at 50° C. and under 20 atmospheres in 12 ml. of a mixture of tetrahydrofuran and methanol (7:3) with 0.8 g. of palladium catalyst (5% on calcium carbonate), until the hydrogen absorption has ceased. The product which precipitates during cooling is dissolved in methylene chloride, filtered off from the catalyst, washed with methylene chloride, and the solvent mixture is removed under vacuum, thus producing 2 g. of 17β-benzoyloxy-3β-methoxymethoxy-5α-androstane, m.p. 118°–120° C.

EXAMPLE 26

1.1 g. of 3β-methoxymethoxy-5-androsten-17-one is hydrogenated as disclosed in Example 25. The thus-obtained crude product is not quite uniform and contains, in addition to 3β-methoxymethoxy-5α-androstan-17-one, of which 0.65 g. can be obtained by crystallization from methanol, also proportions of 3β-methoxymethoxy-5α-androstan-17β-ol. By continuing the hydrogenation or by reduction with sodium borohydride, this product becomes the primary yield.

The preceding examples can be repeated with similar success by substituting the generically and specifically described reactants and/or operating conditions of this invention for those used in the preceding examples.

For example, each of Examples 1 through 9 can be repeated but substituting, respectively, *Microbacterium lactum* IAM-1640; *Protaminobacter alboflavus* IAM-1040; *Bacillus roseus* IAM-1257; *Bacillus sphaericus* ATCC-7055; *Nocardia gardneri* IAM-105; *Nocardi minima* IAM-374; *Nocardia corallina* IFO-3338; *Streptomyces rubescens* IAM-74; Mycobacterium avium IFO-3082; Mycobacterium phlei IFO-3158; *Mycobacterium phlei* (Institute of Health, Budapest No. 29); *Mycobacterium phlei* ATCC-354; *Mycobacterium smegmatis* IFO-3084; *Mycobacterium smegmatis* ATCC-20; *Mycobacterium smegmatis* (Institute of Health, Budapest No. 27), *Mycobacterium smegmatis* ATCC-19979; *Mycobacterium fortuitum* CBS-49566; and Mycobacterium spec. NRRL-B-3683, for Mycobacterium spec. NRRL-B-3805, preferably employing fermentation conditions known in the prior art to be most suited for the submerged fermentative propagation of the selected species of microorganism.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of 17-keto steroids of the androstane series by subjecting a steroid having a sterol hydrocarbon side chain at the 17-position to the oxidative degradation activity of a culture of microorganism which degrades sterol side chains to 17-keto group, the improvement which comprises conducting the fermentation in the absence of an inhibitor whch inhibits attack on the ring system and employing as the starting steroid a sterol 3-acetal of the formula

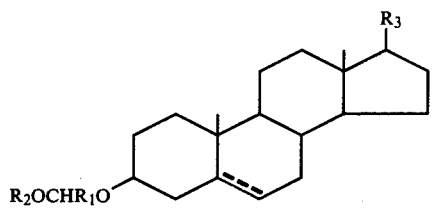

wherein $\equiv\equiv\equiv$ is a single bond or a double bond; $R_1$ is H or lower alkyl, $R_2$ is alkyl, whose chain optionally is interrupted by an oxygen atom; and $R_3$ is a sterol side chain.

2. A process according to claim 1, wherein the starting sterol is a 3-acetal of the formula

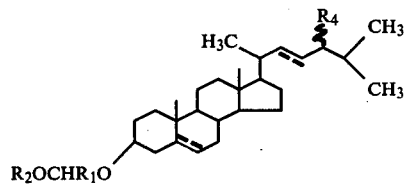

wherein $\equiv\equiv\equiv$ and $R_1$ have the values given therein, $R_2$ is alkyl of 1–4 carbon atoms or alkyl of 3–6 carbon atoms whose chain is interrupted by an oxygen atom and $R_4$ is a hydrogen atom, methyl, or ethyl.

3. A process according to claim 2 wherein $\equiv\equiv\equiv$ in the 5(6)-position is a double bond.

4. A process according to claim 3 wherein $\equiv\equiv\equiv$ in the side chain is a single bond.

5. A process according to claim 4 wherein $R_2$ is $CH_3$ or $C_2H_5$.

6. A process according to claim 5 wherein $R_1$ is H.

7. A process according to claim 1, wherein the microorganism is a member of the genera of Arthrobacter, Brevibacterium, Microbacterium, Protaminobacter, Bacillus, Nocardia or Streptomyces.

8. A process according to claim 7 wherein the microorganisms is of the genus Mycobacterium.

9. A process according to claim 7 wherein the microorganism is Mycobacterium NRRL-B-3805.

10. A process according to claim 2, comprising the further step of cleaving the 3-acetal group of the thus-produced 17-keto steroid in the presence of $H^+$ ions or a Lewis acid, to produce the corresponding 3-hydroxy-17-keto steroid.

* * * * *